United States Patent
Snow et al.

(12) 
(10) Patent No.: US 6,221,673 B1
(45) Date of Patent: Apr. 24, 2001

(54) MATERIALS, METHOD AND APPARATUS FOR DETECTION AND MONITORING OF CHEMICAL SPECIES

(75) Inventors: Arthur W. Snow, Alexandria, VA (US); Henry Wohltjen, Bowling Green, KY (US)

(73) Assignee: MicroSensor Systems Inc., Bowling Green, KY (US)

( * ) Notice: Subject to any disclaimer, the term of this patent is extended or adjusted under 35 U.S.C. 154(b) by 0 days.

(21) Appl. No.: 09/072,283

(22) Filed: May 4, 1998

Related U.S. Application Data

(60) Provisional application No. 60/069,763, filed on Nov. 25, 1997.

(51) Int. Cl.[7] ............................. G01N 33/00; G01N 27/04
(52) U.S. Cl. ........................ 436/149; 436/151; 436/183; 436/139; 436/140; 422/82.01
(58) Field of Search .................................. 436/149, 151, 436/183, 139, 140; 422/82.01, 82.02, 82.03, 82.04, 83, 88, 90, 93, 98

(56) References Cited

U.S. PATENT DOCUMENTS

| | | | |
|---|---|---|---|
| 4,794,089 | * 12/1988 | Mroczkowski et al. | 436/501 |
| 5,141,868 | * 8/1992 | Shanks et al. | 422/82.02 X |
| 5,391,272 | * 2/1995 | O'Daly et al. | 204/153.12 |
| 5,609,907 | * 3/1997 | Natan | 427/2.12 |
| 5,854,078 | * 12/1998 | Asher et al. | 436/133 |

FOREIGN PATENT DOCUMENTS

| | | |
|---|---|---|
| 3604594 | * 8/1987 | (DE). |
| 9810289 | * 3/1998 | (WO). |

OTHER PUBLICATIONS

S. Yamaguchi *Mater. Chem.* 1981, 6, 505–508.*
W.R. Barger et al. *Proc.–Electrochem. Soc.* 1987, 87–15, 198–217.*
M. Brust et al. *J. Chem. Soc. Chem. Commun.* 1994, 801–802.*
K.C. Grabar et al. *Anal. Chem.* 1995, 67, 735–743.*
R.H. Terrill et al. *J. Am. Chem. Soc.* 1995, 117, 12537–12548.*
K.C. Grabar et al. *J. Am. Chem. Soc.* 1996, 118, 1148–1153.*
R.M. Bright et al. *Langmuir* 1996, 12, 810–817.*
D. Bethell et al. *J. Electroanal. Chem.* 1996, 409, 137–143.*
K.C. Grabar et al. *Anal. Chem.* 1997, 69, 471–477.*
M.D. Musick et al. *Chem. Mater.* 1997, A, 1499–1501.*
R.S. Ingram et al. *J. Am. Chem. Soc.* 1997, 119, 9175–9178.*

* cited by examiner

Primary Examiner—Arlen Soderquist
(74) Attorney, Agent, or Firm—Whitman Breed Abbott & Morgan LLP

(57) ABSTRACT

A method for investigating a target environment to determine whether or in what amount a chemical species may be present therein, which comprises: (a) exposing to said environment an article of manufacture comprising a multiplicity of particles in close-packed orientation, said particles having a core of conductive metal or conductive metal alloy and deposited thereon a ligand which is capable of interacting with said species such that a property of said multiplicity of particles is altered; (b) subjecting said multiplicity of particles to conditions sufficient for said property to be exhibited; and (c) monitoring said property to determine whether there is, or the amount of, any change as an indication of whether, or in what amount, said species is present; a multiplicity of particles suitable for use in such method; and equipment suitable for implementing the method.

11 Claims, 9 Drawing Sheets

MATERIALS, METHOD AND APPARATUS FOR DETECTION AND MONITORING OF CHEMICAL SPECIES

This application claims the benefit of U.S. Provisional No. 60/069,763 filed Nov. 25, 1997.

FIELD OF THE INVENTION

The invention relates to the detection or quantitation of a chemical species in a target environment, and the discovery that the properties of certain particles which are interactive with the chemical species can advantageously be monitored as a indication or in which amount the species is present.

BACKGROUND OF THE INVENTION

There are a number of known approaches to determining the presence or amount of a chemical species in a target environment by exposing a substance capable of interacting with the species to such environment and monitoring a change in a property of the substance due to such interaction as an indication of whether or in what amount the species is present.

One such approach has been the exposure to the environment of a species-interactive substance applied to a piezoelectric substrate. The substance is affected such that, if any of the species present, a preselected property of the substance is changed. A surface acoustic wave is induced in the piezoelectric material. Any change of property in the substance results in an attenuation of the surface acoustic wave, which can be monitored as an indication of whether or in what amount the species is present. For instance, see U.S. Pat. Nos. 4,312,228 and 4,759,210.

Another approach has been the provision of a capacitive device for detecting the presence or measuring the concentration of an analyte in a fluid medium. A plurality of interdigitated fingers formed from metallic conductors are placed upon an insulating substrate. The substrate may be made from an insulating material such as glass and the fingers may be made of copper and gold; the fingers are covered with an insulating passivation layer. The approach involves biospecific binding between a biochemical binding system and the analyte to change the dielectric properties of the sensor. See U.S. Pat. No. 4,822,566.

Yet another approach has been the provision of a chemical sensor comprising a thin film of dithiolene transition metal complexes applied to a chemiresistor device. The film is deposited upon an interdigitated electrode on a substrate. The film changes conductivity when exposed to a chemical gas or vapor of analytical interest. The interdigitated electrodes may be gold and the substrate is an insulating material such as quartz. A power supply and current measuring device are included. See U.S. Pat. No. 4,992,244.

Still another approach has been provision of a biosensor in the nature of a sample testing device that includes an electrode structure which makes measurements of one or more electrically measurable characteristics of the sample. The area between two electrodes on one wall of the test cell can be coated with a binding agent which can bind conducting particles such as gold sol particles. See U.S. Pat. No. 5,141,868.

A different type of biosensor which has also been suggested has a thin crystalline drive surfactant polymeric electrically conducting layer to which may be bound members of specific binding pairs. Binding of an analyte or reagent to the binding pair member layer may change electrical properties of the layer for measurement of the analyte. See U.S. Pat. No. 5,156,810.

However, it would still be desirable for the art to have an alternative detection technology which lends itself to ready and versatile implementation as well as consumes power at a very low level, without sacrificing reliability, miniaturization affinity, and low cost.

OBJECTS OF THE INVENTION

It is an object of the invention to provide sensitive and reliable technology for the detection and monitoring of chemical species.

It is another object of the invention to provide materials, methods and equipment suitable for the sensitive and reliable detection or quantitation of a preselected chemical species in a target environment.

It is yet another object of the invention to provide materials, methods and equipment as aforesaid which are well-suited for applications requiring compact size, low cost and low power consumption.

It is a further object of the invention to provide methods of fabricating the aforementioned equipment.

SUMMARY OF THE INVENTION

In one aspect, the invention is in an article of manufacture suitable for use in determining whether or in what amount a chemical species is present in a target environment, which article comprises a multiplicity of particles in close-packed orientation, said particles having a core of conductive metal or conductive metal alloy, in each said particle such core being of 0.8 to 40.0 nm in maximum dimension, and on said core a ligand shell, of thickness from 0.4 to 4.0 nm, which is capable of interacting with said species such that a property of said multiplicity of particles is altered.

In a further aspect, the invention is in a method of investigating a target environment to determine whether or in what amount a chemical species may be present, which comprises: (a) exposing to said environment an article of manufacture comprising a multiplicity of particles in close-packed orientation, said particles having a core of conductive metal or conductive metal alloy and deposited thereon a ligand which is capable of interacting with said species such that a property of said multiplicity of particles is altered; (b) subjecting said multiplicity of particles to conditions sufficient for said property to be exhibited; and (c) monitoring said property to determine whether there is, or the amount of, any change as an indication of whether, or in what amount, said species is present.

In another aspect, the invention is in an assembly suitable for investigation of a target environment to determine whether or in what amount a chemical species may be present, which comprises: (a) a substrate suitably configured for presenting a multiplicity of particles supported thereon to contact with said environment; (b) supported by said substrate, a multiplicity of particles in close-packed orientation, said particles having a core of conductive metal or conductive metal alloy and deposited thereon a ligand which is capable of interacting with said species such that a property of said multiplicity of particles is altered; and (c) a sensor for monitoring said property of said multiplicity of particles.

In yet another aspect the invention is in a method of fabricating an assembly suitable for investigation of a target environment to determine whether or in what amount a chemical species may be present, which comprises depositing on a substrate (i) a pair of interdigitated electrodes each having a comb-like configuration and (ii) in such manner that the electrodes are electrically connected, a thin film of a multiplicity of particles having a core of conductive metal or conductive metal alloy, in each said particle the core being from 0.8 to 40.0 nm in maximum dimension, and deposited on said core a ligand shell, of thickness from 0.4 to 4.0 nm, which is capable of interacting with said species such that a property of said multiplicity of particles is altered.

In still a further aspect the invention in a system suitable for investigating a target environment to determine whether or in what amount a chemical species may be present, which comprises: (a) a multiplicity of particles in close-packed orientation, said particles having a core of conductive metal or conductive metal alloy and deposited thereon a ligand which is capable of interacting with said species such that a property of said multiplicity of particles is altered; (b) means for exposing said multiplicity of particles to said environment; (c) means for subjecting said multiplicity of particles to conditions sufficient for said property to be exhibited; and (d) means for monitoring said property to determine whether there is, or the amount of, any change in such property as an indication of whether or in what amount said species is present.

By the term "close-packed orientation" herein we mean a solid-state arrangement of nanoscale metal particles as aforesaid, wherein ligand shells are in contact with their nearest neighbors and in which multimolecular sized (for example, 0.1 to 1.0 nm) voids among the particles are interconnected. A particle is typically "stabilized" in that the metal core of the particle is effectively encapsulated by the ligand shell.

Practice of the invention results in substantial advantages. The multiplicity of particles is effective in extremely small amounts, and thus the method and equipment embodiments which utilize such multiplicity of particles can be implemented on a commensurately small scale. Furthermore, the multiplicity of particles is extremely sensitive in detection applications. Additionally, by varying the ligand component, the metal core size or type and the ligand shell size or type, the multiplicity of particles can be made highly sensitive to interaction with, and thus detection of, a wide range of chemical species. Consequently, the method and equipment embodiments which involve such multiplicity of particles are also highly sensitive and highly adaptable. Moreover, fabrication and use of a sensor assembly or system in accordance with the invention is relatively simple and relatively inexpensive; for instance, the sensor assembly can readily be interfaced with inexpensive electronic read-out devices, and its operation requires very little electrical power. Also, due to simplicity of design, the sensor assembly and system are rugged and dependable. Other design-based benefits are the achievability of rapid, linear and reversible response, and versatility such that the environment investigated and the chemical species to be detected via the invention can be solid (e.g., porous solid), liquid or gaseous. And, when using embodiments which incorporate both a sensor component and a reference component, the invention further is temperature-compensated and tolerant of production variations.

DESCRIPTION OF CERTAIN PREFERRED EMBODIMENTS

Figure 1:
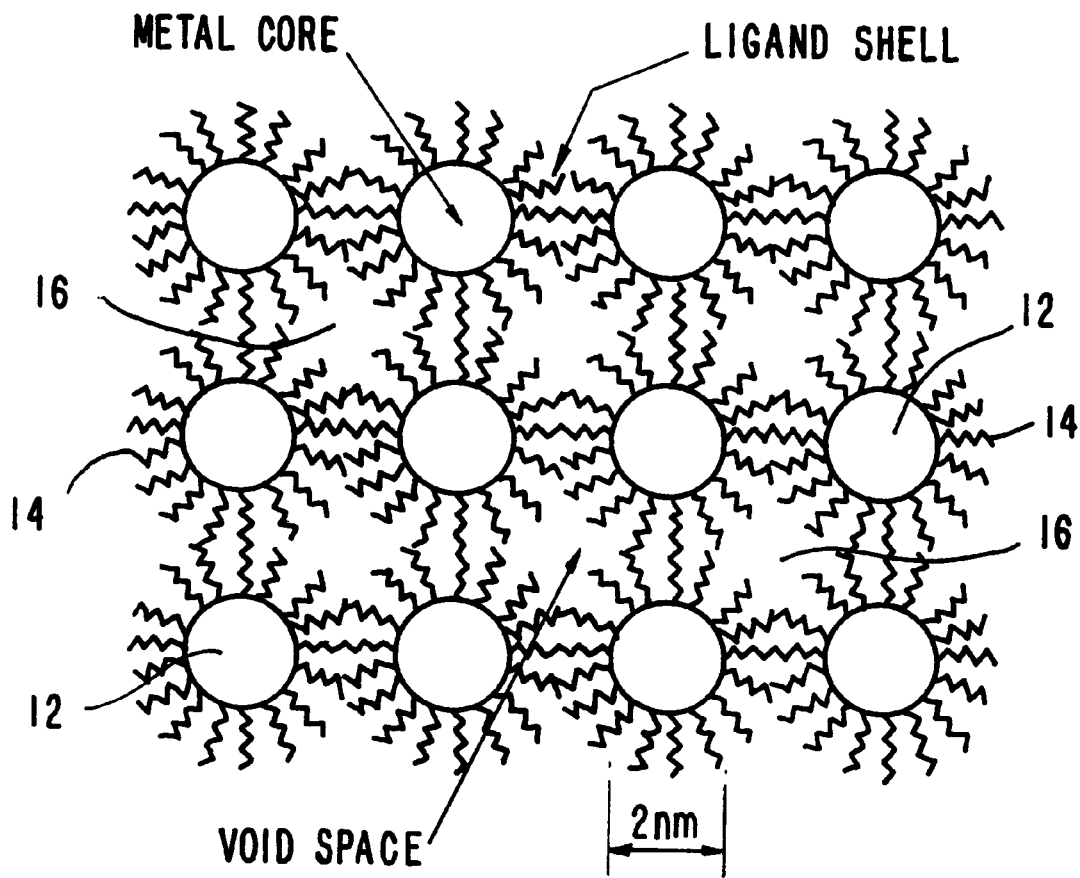
FIG. 1 is a schematic depiction of particles arranged in close-packed orientation according to the invention.

A central feature of the invention is a multiplicity of particles in close-packed orientation, as aforesaid. Each of the particles is an extremely small cluster of conductive metal atoms that forms a metallic "core" surrounded by a thin "ligand shell" of relatively non-conductive material chemically (e.g., covalently) bound to the core.

The cluster of metal atoms can be composed of a single conductive metal, or of atoms of two or more conductive metals. Suitable conductive metals are metals capable of being processed on a nanoscale and of bonding to a thin insulating ligand shell to form a stabilized metal particle, a multiplicity of which particles is stable in respect of ambient environments and exhibits a stable and measurable electrical conductivity. Examples are noble metals or other conductive metals such as copper, nickel and tin. The elemental metal core is illustratively a noble metal, preferably silver, gold, platinum or palladium. The metal alloy core is illustratively a combination of two or more noble metals, such as two or more of silver, gold, platinum and palladium. The core bodies are advantageously spherical or spheroidal, though they can also be of other regular shapes, or irregular in shape; as will be apparent the shape of the particle typically simulates the shape of the core. Also, typically, the metal cluster core will range from 0.8 to 40 nm (preferably 2 to 20 nm) in maximum dimension; the core is advantageously spherical, in which case its typical size is radius of from 0.4 to 20 nm, preferably 1 to 10 nm.

The encapsulating ligand shell is advantageously an organic, inorganic or combined organic/inorganic substance which is preselected for its ability to interact with the chemical species of interest such that the ligand shell is changed in a manner perceptibly affecting a property of the multiplicity of particles, with the result that the species can be detected if present. The ligand molecule typically has a head-tail type structure; the head is a functional group possessing a bonding interaction with metal atoms in the core surface, and the tail has a structure and composition designed to provide additional stabilization of metal clusters (i.e., core bodies) against irreversible agglomeration, induce solubility in solvents and promote interactions with chemical species of interest. The ligand shell can be a monomolecular or multimolecular layer. The ligand shell substance is advantageously a functionalized organic compound, such as a thiol, or an amine. These thiols can be primary aliphatic thiols (preferably straight chain or branched), secondary aliphatic thiols, tertiary aliphatic thiols, aliphatic thiols substituted heterofunctionally (for instance, by OH, COOH $NH_2$, Cl, and the like, preferably $HS(CH_2)_6OH$ or the hexafluoroacetone adduct) aromatic thiols, aromatic thiols substituted heterofunctionally (for instance, by OH, COOH $NH_2$, Cl, and the like, preferably $HS(CH_2)_6OH$ or the hexafluoroacetone adduct) and araliphatic thiols substituted heterofunctionally (for instance, by OH, COOH $NH_2$, Cl, and the like, preferably $HS(CH_2)_6OH$ or the hexafluoroacetone adduct). Preferred amines are primary aliphatic amines. The aliphatic portions of such thiols and amines can be of from 3 to 20 carbon atoms, especially 4 to 16 carbon atoms.

The shell is advantageously neither so thin that the multiplicity of particles is effectively metallic in its conductivity properties, nor so thick that the multiplicity of particles is completely electrically insulating. Preferably, such thickness ranges from 0.4 to 4 nm, especially 0.4 to 2.5 nm. The organic ligand shell stabilizes the metal cluster against irreversible coagulation and also imparts a high solubility of the cluster complex in organic solvents. This allows for a processibility of these materials as thin films as discussed hereinafter.

Once in possession of the teachings herein, one of ordinary in the art will be able to prepare the subject particles by dissolving a salt of the conductive metal—or in the case of an alloy, salts of the conductive metals—of which the core is to be composed, and an organic substance corresponding to the desired ligand, in a common solvent and subsequently adding a reducing agent under conditions of rapid mixing (see M. Brust et al., J. Chem. Soc., Chem. Comm. 1994, 801; D. V. Leff et al, Langmuir 1996, 12, 4723). The metal ions of the salt(s) are reduced to neutral atoms and subsequently nucleate to form multiatom core bodies. These core bodies grow by absorption of additional metal atoms. Competitively, the organic ligand molecule is absorbed on the growing metal core body surface, encapsulates the metal core body and terminates its growth. The relative concentrations of the metal salts and organic ligand molecules determine the relative rates of metal core body growth and organic ligand encapsulation, and thus the size of the metal core in the stabilized particle. The thickness of the ligand shell is determined by the size of the ligand molecule. It is important that there be a strong chemical interaction between the ligand molecule and neutral metal otherwise the metal core bodies will coagulate and not redisperse. The choice of a suitable ligand molecule is within the skill of the art once the practitioner is in possession of the teaching set forth herein. By way of example, sulfur compounds are particularly effective for coordination to gold, silver, platinum and copper metals. Amines have a weaker but sufficient interaction with gold. In principle, any combination of reducible metal ion and organic ligand, with a sufficient neutral metal to ligand chemical interaction, can form coated metal clusters—i.e., particles—useful in this invention. In other embodiments of the invention alternative synthetic methods can be utilized. For instance, the metal ion reduction can be conducted initially and the deposition of the ligand shell thereafter. This can involve generation of the metal particles in vacuo or in liquid suspension with subsequent formation of the ligand shell by addition of the ligand shell molecules.

A chemical sensor assembly is made when a large ensemble (i.e., a multiplicity) of these particles in close-packed orientation, as aforesaid, is deposited onto a surface equipped with a sensor component, for example, a pair of electrical contacts. The resulting "device" can be described as a series of metal-insulator-metal (MIM) junctions, where the metal is the core and the insulator is the ligand shell. Sometimes herein the invention is referred to as a "metal-insulator-metal ensemble" ("MIME") device. A multiplicity of particles in close-packed orientation is shown in FIG. 1. Each particle has a conductive metal core 12 and a ligand shell 14, with void space 16 interspersed among the particles. Variations in the core size and ligand shell thickness produce significant changes in the sensitivity to chemical species.

Both the target environment which is being investigated, and the chemical species of interest if present, can be in the vapor, liquid or solid phase. In this connection, it should be noted that the environment can be a pure substance (e.g., if the environment is entirely constituted of the chemical species or is devoid of the chemical species) or a combination of substances (e.g., a multi-component gas, liquid or solid system, or a heterogeneous system containing substances in two or more different phases). When the multiplicity of particles is contacted with such environment the ligand material interacts with—for instance, sorbs—the species if it is present. This causes a change in the ligand material and a change in one or more properties of the multiplicity of particles. Variations in the chemical composition of the ligand shell produce significant changes in chemical selectivity. Any one of a variety of properties of the multiplicity of particles can be monitored, the only requirement being that the property change as a function of the interaction of the ligand material with the chemical species (if present). In several good embodiments of the invention an electrical property, such as conductivity, is monitored. In other good embodiments, an optical property is monitored (due to the regular spacing of reflective metal centers, optical property changes should result from the swelling of the particles as a consequence of interaction with the chemical species). The identification of properties to be monitored is within the skill of the art, once those in the art are in possession of the teachings herein.

Formation of the multiplicity of particles as a thin film is a sensitive operation. In our experience, casting from solution with slow evaporation does not produce a thin film with reproducibility or acceptable uniformity. We have invented various methods that address this problem. For example, a first technique is spraying a solution as a fine mist from an air brush onto a substantial surface which has been heated, preferably to a temperature above the boiling point of the solvent. The solvent is flashed away leaving a film of very fine uniformly dispersed features. Without heating the features of the film are very coarse and nonuniform. Another technique is based on chemical self-assembly. The sensor surface and substrate are cleaned by a plasma or chemical treatment and coupling agents are applied. Coupling agents are difunctional molecules with an inert spacing structure separating the functional groups (e.g. an a-ω silyl alkanethiol, such as $(CH_3O)_3Si(CH_2)_3SH$, or a dithiol, $HS(CH_2)_6SH$)). One functional group bonds to the sensor/substrate (e.g., the $—Si(OCH_3)_3$ or the —SH functional group) surface, and the other (e.g., a second —SH functional group) is oriented away from the surface for subsequent bonding with the multiplicity of particles. The ligand shell of the metal particle is a dynamic system where an individual molecule may be displaced by a similarly functionalized molecule. Thus, the immobilized thiol group of the absorbed coupling agent may bond to a particle and immobilize it on the aforementioned surface. In this fashion a monolayer of particles is chemisorbed on the surface. Subsequently, the immobilized particle monolayer is exposed to a solution of a dithiol coupling agent. The dithiol exchanges with some of the monofunctional thiol ligand molecules in the immobilized particle ligand shell and positions the second thiol group on the outer surface of the immobilized particle's ligand shell. A second exposure to a solution for forming the stabilized multiplicity of particles results in chemisorption of a second particle layer on the first. In this manner many layers of particles are built up into a multilayer film. This offers a very highly controlled, uniform and reproducible deposition where variations in the character of metal core and ligand shell molecule may be made at any desired depth in the cluster multilayer. As an additional benefit, this film is not removable by solvents or by mild abrasion unlike that of the first technique.

Figure 2:
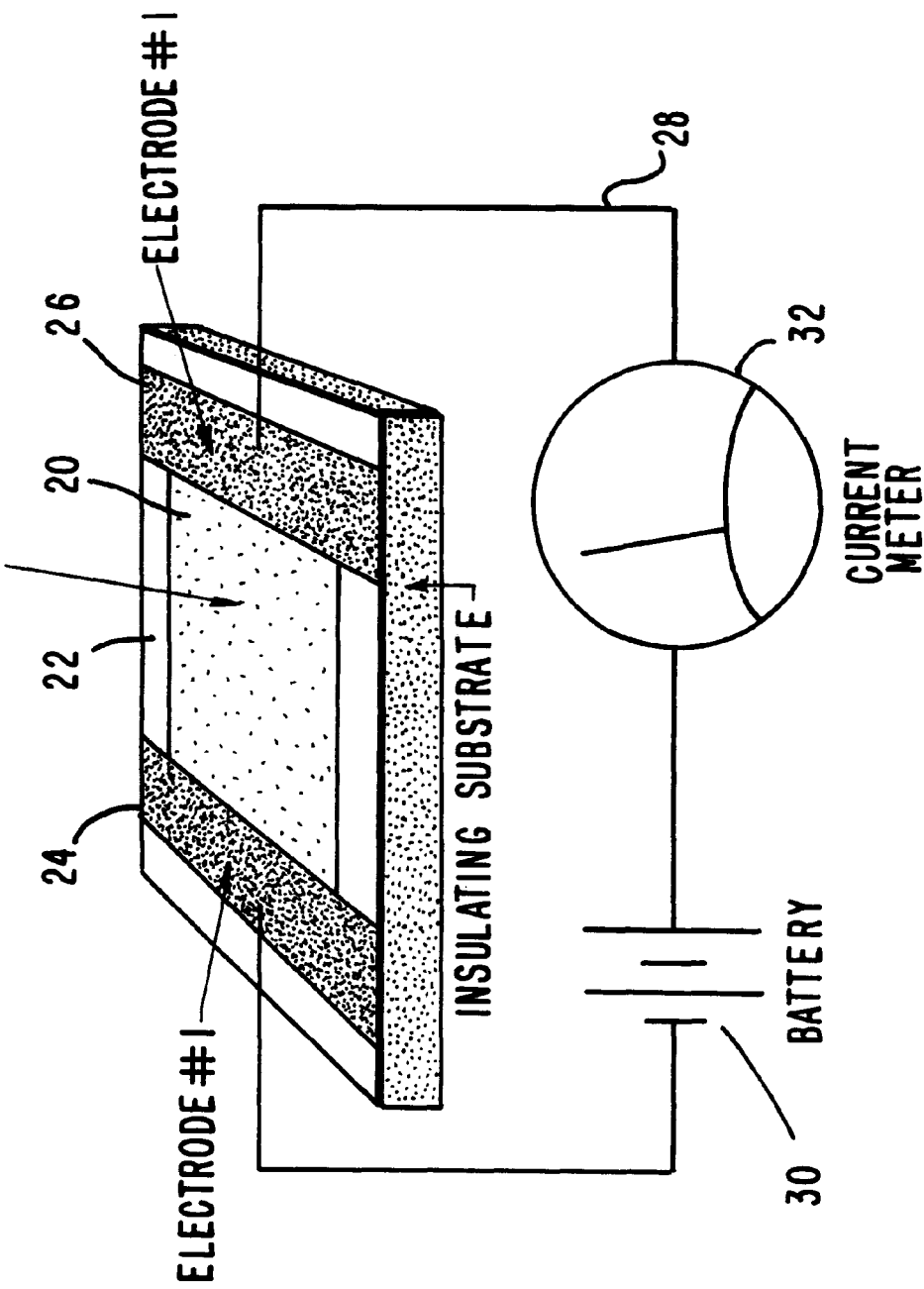
FIG. 2 is a schematic depiction of a basic sensor system in accordance with the invention.

In one basic preferred embodiment the invention provides an assembly utilizing the aforementioned thin film which assembly comprises a pair of electrodes connected by a thin film of the MIME material. Such an arrangement is shown in FIG. 2. An MIME thin film 20 is formed on a substrate 22 so as to connect two electrodes 24, 26 also formed thereon. A circuit 28 including a battery 30 and current meter 32 is used to measure the electrical conductivity of the MIME device. Conductivity can be measured under AC or DC conditions.

Figure 3:
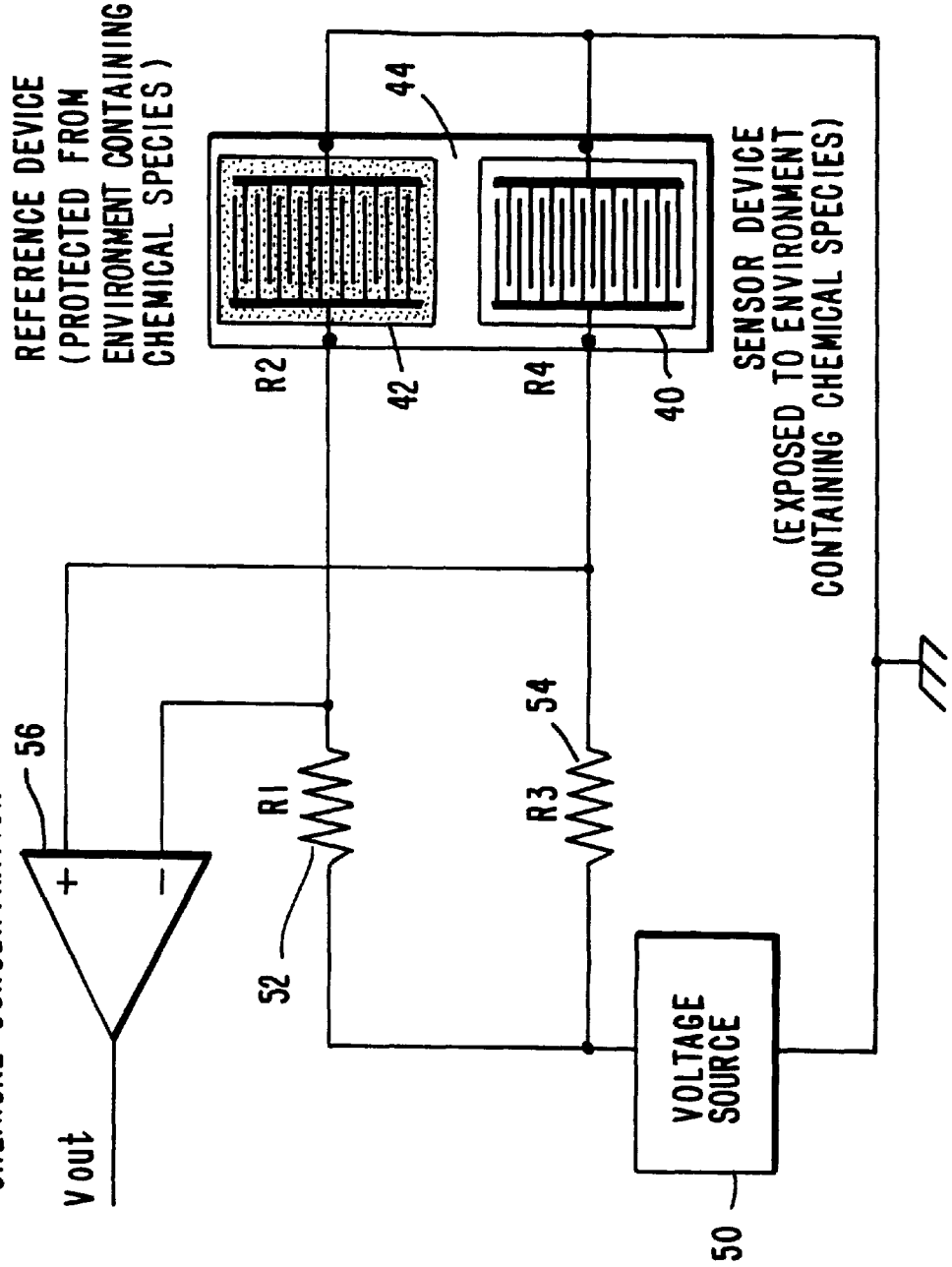
FIG. 3 is a schematic depiction of another sensor system according to the invention, which system includes both a sensor component and a reference component.

An even more preferred embodiment is a pair of lithographically patterned (e.g., via photolithography, silk-screening, etc.) devices. The pattern results in planar interdigital "comb" electrodes having a large ratio of electrode perimeter to electrode spacing. The large length-to-cross-sectional-area ratio serves to decrease the electrical resistance of the device, thereby making it very easy to measure any conductivity variation with low noise and high precision. In a further preferred embodiment, there is a matched pair of these interdigital devices, fabricated simultaneously on the same substrate. As shown in FIG. 3, sensor device 40 and reference device 42 are formed on substrate 44. Each such device comprises a pair of interdigitally oriented electrodes. A multiplicity of particles in accordance with the invention is deposited between and in contact with the electrodes of each pair. The devices are connected in a circuit 48 containing a voltage source 50 and resistors 52, 54, and the output signals from the devices fed to a comparator 56. Sensor device 40 is exposed to an environment containing chemicals to be measured (e.g., gas, liquid or solid), and reference device 42 is covered with a passivating layer (e.g., plastic, glass, paraffin wax, etc.), or in some other way is isolated from the environment possibly containing the chemical species of interest. The reference device provides a means to compensate for the normal change in resistance with temperature exhibited by the MIME in thin film applications. By fabricating the sensor and reference devices simultaneously, one is assured of accurate matching and highly reproducible system performance even if the lot-to-lot production process varies substantially.

In a typical MIME device film thickness is 5 to 10,000 nm. The composition of the MIME thin film and the geometry of the electrode on which it is deposited, are selected to provide an attractive baseline resistance (e.g., 10,000 Ω) to permit high precision measurement of conductivity changes with simple electronic circuitry. Exposure of the film to low concentrations (e.g., 100 ppm by volume) of chemical vapors can change the conductivity by several percent. This is a very large change if temperature effects can be nulled out by using a reference device such as the one disclosed in this invention. Indeed, it is quite easy to measure resistance change in 1 part of $10^5$ (i.e., ±0.001%) with this sensor/reference combination. Thus, monitoring trace level (e.g. sub-ppm) concentrations of many vapors is readily achievable.

The linearity and sensitivity of the MIME sensor are illustrated in FIGS. 5 through 8.

Figure 4:
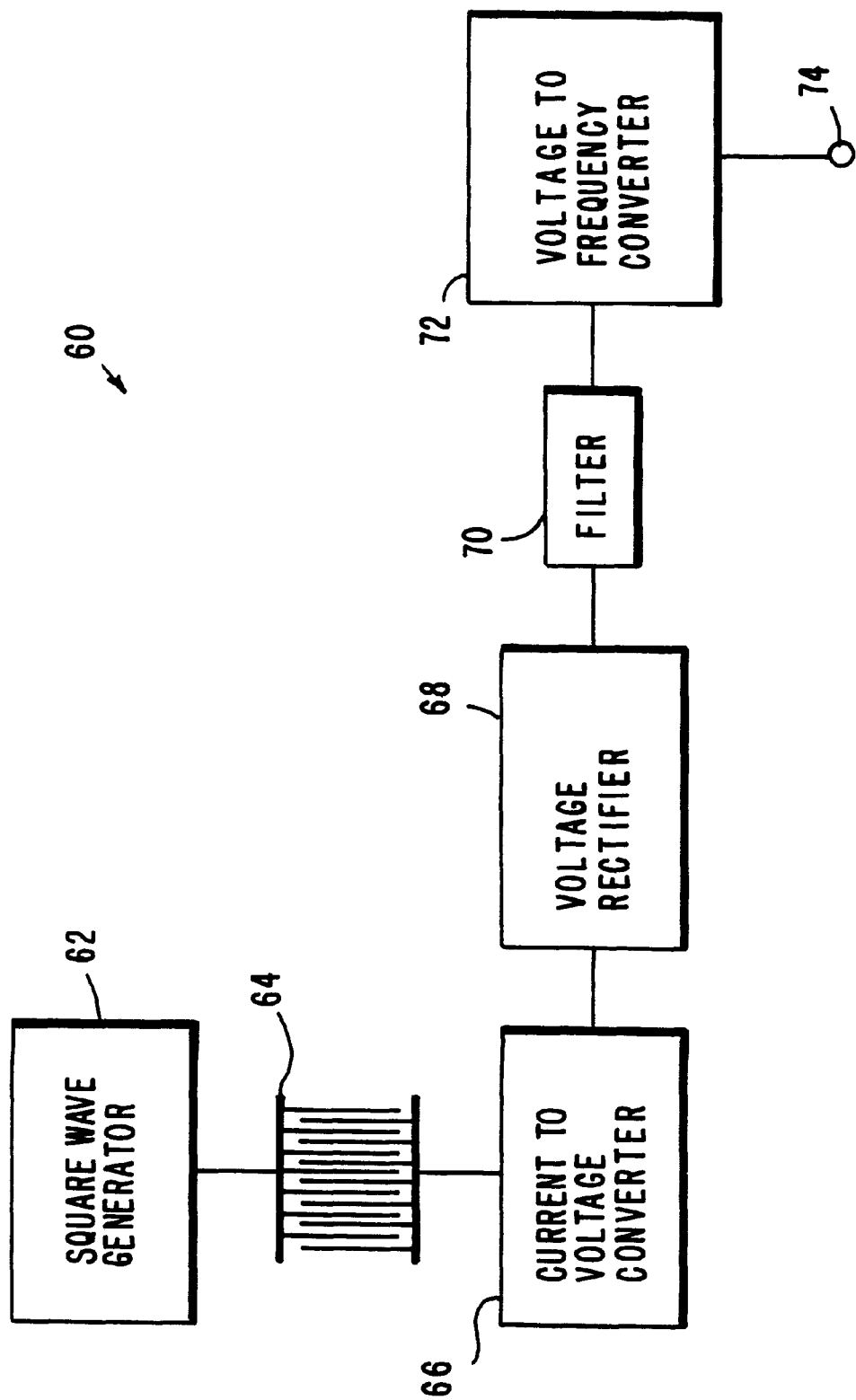
FIG. 4 is a schematic depiction of a sensor system in accordance with the invention.

FIG. 4 illustrates a testing apparatus 60 implementing a MIME sensor 64 according to the present invention. Apparatus 60 includes a square wave generator 62, a MIME sensor 64, a current-to-voltage converter 66, a voltage rectifier 68, a filter 70, and a voltage-to-frequency converter 72.

Square wave generator 62 is a conventional wave generator for producing a square waveform signal preferably at a frequency of 100 Hz and having an amplitude of less than 0.5v. Current-to-voltage converter 66 is a conventional device for converting a supplied current into a voltage preferably having a range between −5v and +5v. Preferably, the output of converter 66 changes by 1 mv in response to each nanoampere of change in input current. Voltage rectifier 68 is a conventional rectifier device preferably adapted for half-wave rectification. Filter 70 is a conventional filter device for filtering transients from a signal and is preferably comprised of a low-pass filter. Voltage-to-frequency converter 72 is a conventional voltage-to-frequency conversion device and preferably produces a 350 Hz change in output frequency in response to each millivolt of change in input voltage. The output signal of converter 72 is detected at output node 74.

MIME sensor 64 comprises particles of gold core having a nominal radius of 1 nanometer combined with an alkanethiol ligand shell having 8 carbon atoms in the alkane chain. A film of this core-ligand material approximately 0.4 micrometers in thickness was sprayed onto a small interdigital electrode component consisting of 50 "finger pairs" of gold 15 $\mu$m wide and spaced 15 $\mu$m from the next element to form sensor 64. The finger aperture was 4800 $\mu$m. The gold microelectrode component was lithographically fabricated on an insulating substrate of quartz.

In operation, MIME sensor 64 was excited with an AC square wave having an amplitude of less than 0.5 V and a frequency of 100 hz produced by generator 64. Current flowing through sensor 64 was converted into a voltage by current-to-voltage converter 66. The resulting AC voltage was rectified by rectifier 68, filtered by filter 70, and then presented to voltage-to-frequency converter 72. Converter 72 produced an output signal which could be detected at node 74. Thus, AC conductance changes in MIME sensor 64 were converted into frequency changes that were easily recorded using a laboratory data acquisition system. This approach is not necessary in order to practice this invention but was convenient for our particular laboratory set-up.

Figure 5:
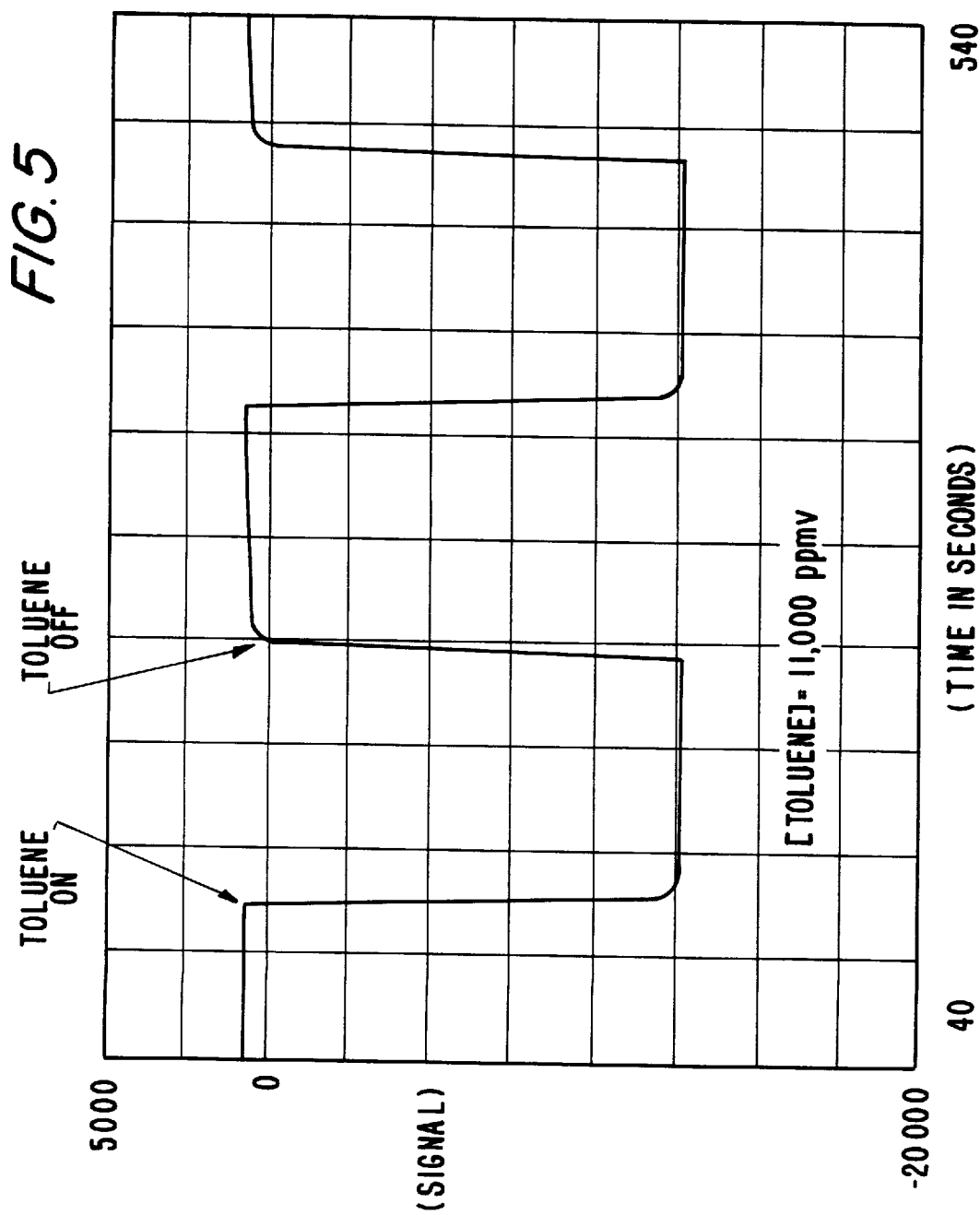
FIG. 5 is a plot of signal v. time response showing the variation in resistivity, upon exposure to toluene vapor, for the system depicted in FIG. 4.
Figure 6:
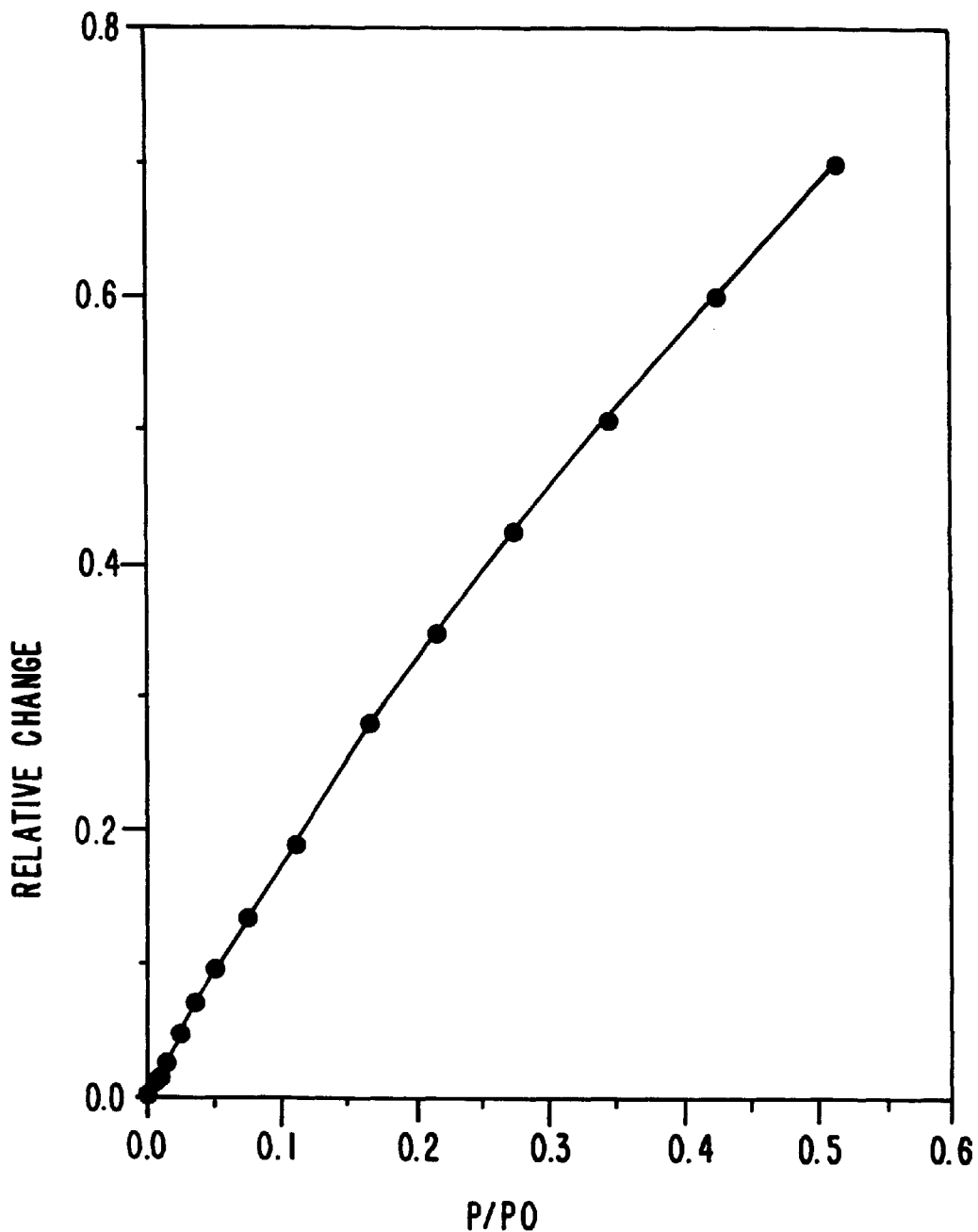
FIG. 6 is a plot of toluene content v. resistivity showing change in the latter which results from change in toluene content for the system depicted in FIG. 4.
Figure 7:
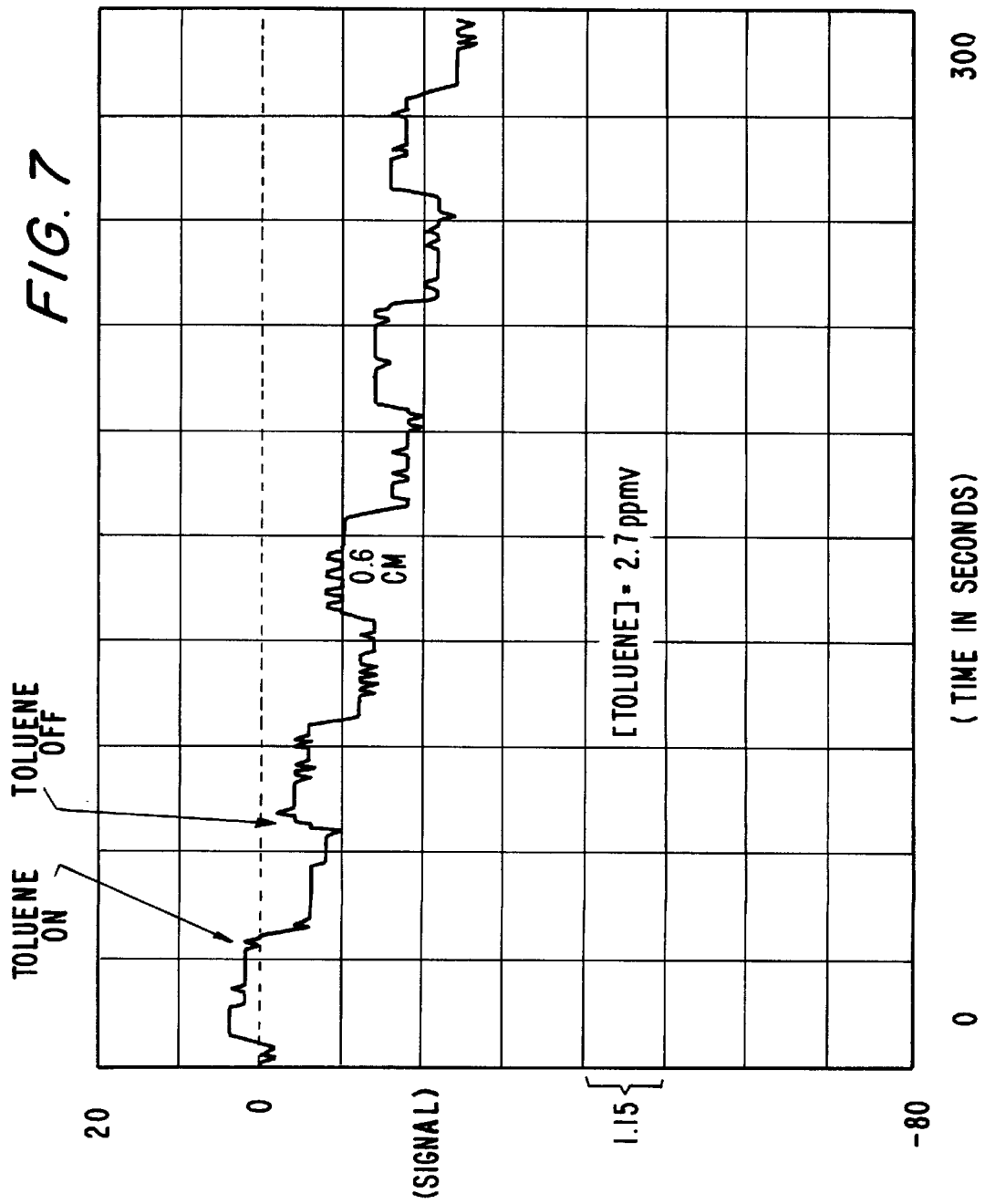
FIG. 7 is a plot of signal v. time response as a function of the presence of toluene for the system depicted in FIG. 4.
Figure 8:
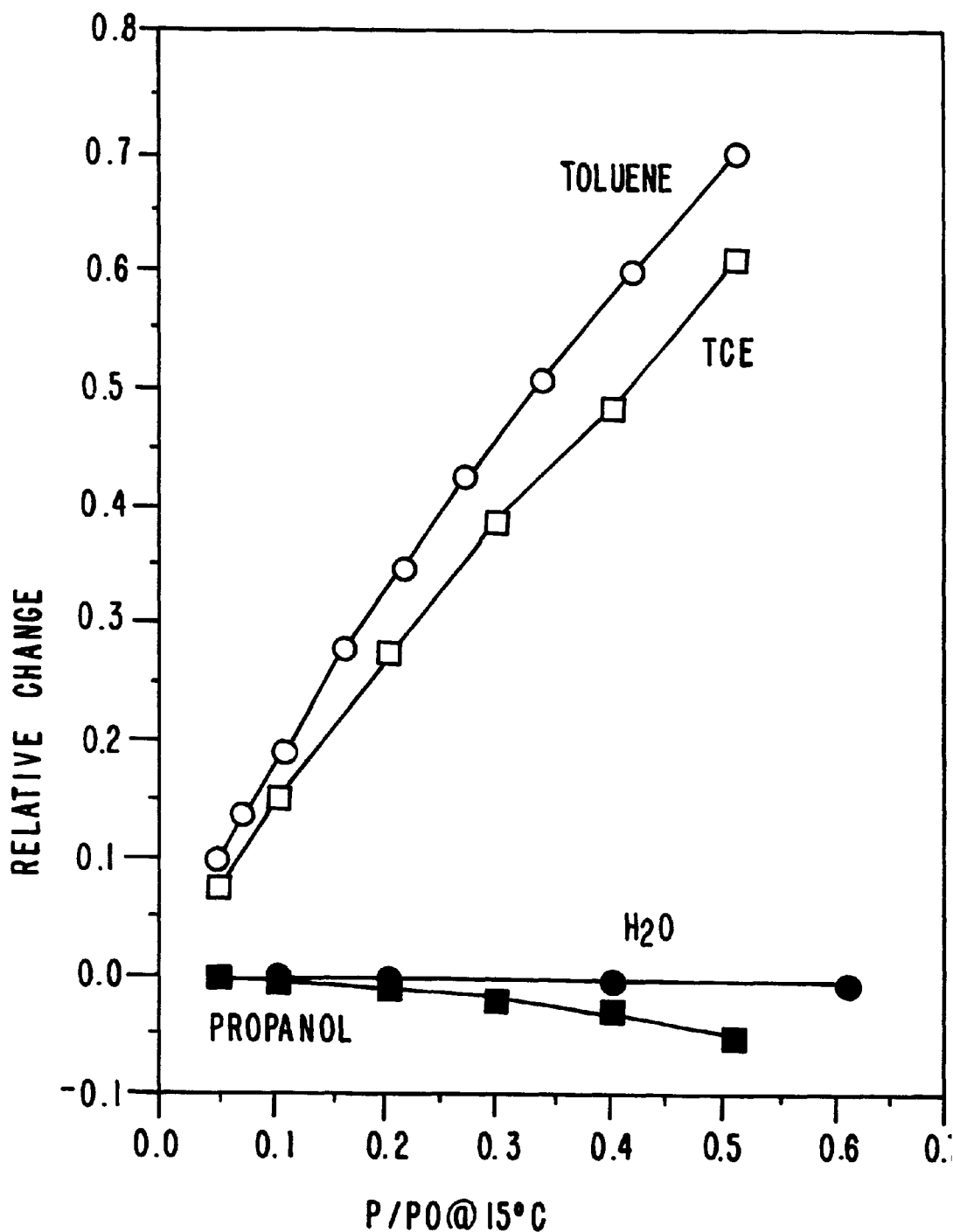
FIG. 8 is a plot of chemical species content v. resistivity showing the change in resistivity which results from a change in content of several different substances for the system depicted in FIG. 4.

The relative resistance change of the device upon exposure to toluene vapor is shown in FIG. 5. The responses are rapid and reversible. FIG. 6 shows the highly linear behavior of the device over a wide range of concentrations. FIG. 7 shows the ability of the MIME sensor to detect trace quantities (e.g., sub parts-per-million by volume concentration) of toluene vapor. FIG. 8 compares the sensitivity of the device to a variety of other vapors. Of great significance is the extraordinarily low response to water vapor which is essential for practical application in which trace levels of organic vapors must be detected and monitored in humid ambient air.

Figure 9A:
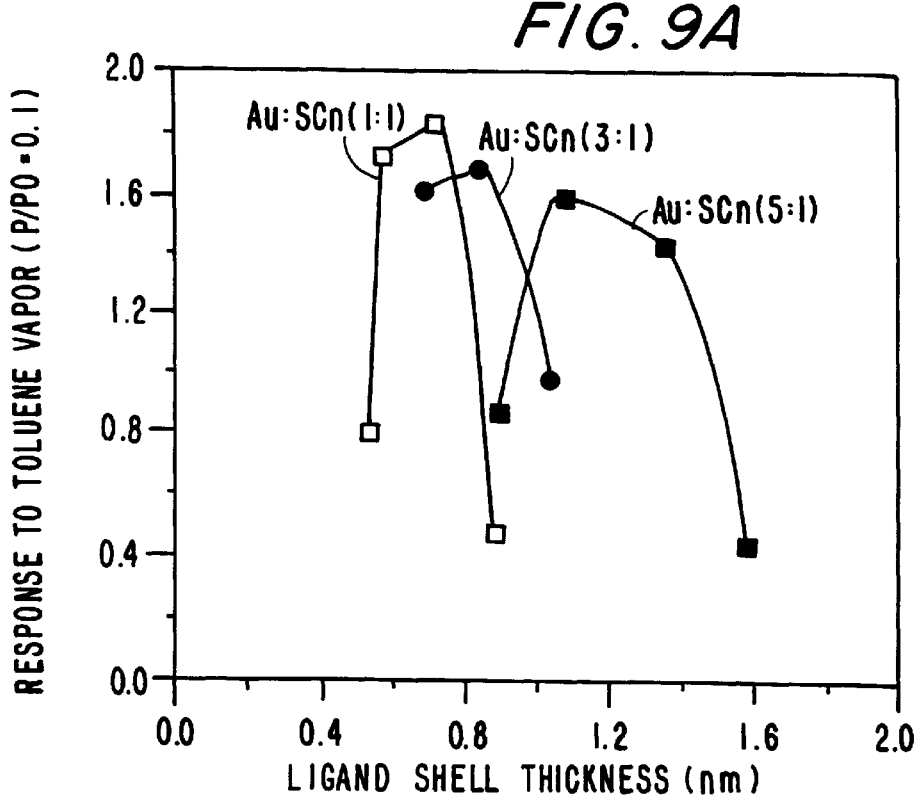
FIGS. 9A and 9B are, respectively, a plot of ligand shell thickness of various particles v. the response of a multiplicity of such particles to changes in toluene content, and a plot of particle core radius for various particles v. the response of a multiplicity of such particles to changes in toluene content.
Figure 9B:
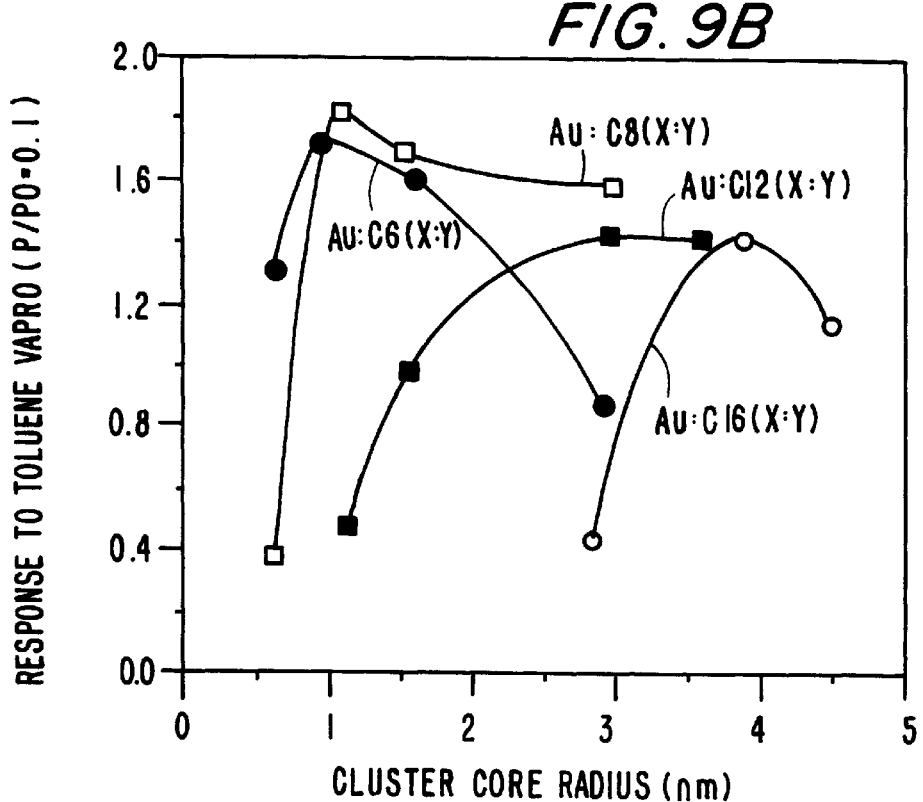

The sensitivity of the MIME device is related to the nanometer size of the encapsulated metal cores, the overall size of which should not be greater than 48 nm in maximum dimension. The size of the metal core and thickness of the ligand shell jointly determine the achievable sensitivity. As an example, FIGS. 9A and 9B display two plots relating toluene vapor sensitivity to these two parameters, respectively, for a normal alkanethiol stabilized gold core system (abbreviated Au:SCn(X:Y), wherein n refers to the number of carbon atoms in the normal alkanethiol ligand molecule and (X:Y) refers to the gold:alkanethiol stoichiometry used in the synthesis). The upper plot presents the toluene vapor response (at a vapor concentration corresponding to P/Po=0.1) of devices prepared with three homologous series of clusters having constant metal core radii (determined by the (X:Y) where (1:1), (3:1) and (5:1) correspond to 1.11 nm, 1.57 nm and 2.97 nm, respectively) and varying ligand shell thickness. The maxima of this plot show that each metal core size has an optimum ligand shell thickness for highest sensitivity. This maximum sensitivity gradually diminishes as one progresses to homologous series of larger radii. The lower plot of FIG. 9 presents the toluene vapor response of devices prepared with homologous series of clusters having constant ligand shell thicknesses (determined by Cn where C6, C8, C12 and C16 correspond to 0.71 nm, 0.86 nm, 1.16 nm and 1.58 nm, respectively) and varying core radii. This plot also indicates that maximum sensitivity correlates with an optimum core size and ligand shell combination and that the overall sensitivity gradually diminishes as the core size progresses to 20 nm. Typically, the range of effective dimensions for the stabilized metal clusters is 0.4 to 20 nm for the core radius and 0.4 to 4 nm for the ligand shell thickness.

Sensitivity can also be chemically modulated by introduction of a heterofunctionality to the ligand shell or by adding a binder with heterofunctionality just prior to the deposition of the film. The heterofunctionality is a heteroatom functional group such as amine, hydroxyl, halogen, phosphoryl, carboxy, ether, etc. In the former case, the ligand molecule is then bifunctional, one functional group to bind with the metal core surface and the other to provide an attractive interaction for sorption of target species. In the latter case, a binder such as a polymer is codissolved with the particle component precursors and simultaneously deposited on the sensor and substrate. The heterofunctionality in the binder then provides the attractive interaction for sorption of target vapors as in the former case above.

The following test procedures and parameters are useful in practice of the invention:

Weight Fraction Metal

A thermogravimetric analysis (TGA) measurement of the metal weight fraction in the core/shell composite is conducted using standard thermal analysis equipment with conditions of a 10 to 20 mg sample, a 20° C./min heating rate from 25 to 600° C. in a nitrogen atmosphere. The determination is based on the fraction of unvolatilized mass at 600° C. In samples analyzed here the organic mass fraction is completely volatilized at temperatures of 400° C. or below, and the residual mass (metal component) is constant from 400 to 600° C.

Cluster Core Radius

This is a microscopic parameter describing the metal core size. For instance, with gold complexes it is calculated from a spherical model relating the core size to the alkanethiol monolayer coverage (see R. H. Terrill et al, J. Amer. Chem. Soc. 117, 12537 (1995)). The model assumes a hexagonal closest packed arrangement of surface gold atoms with two of three gold surface atoms chemically bonded to individual organic ligands of the ligand shell. Adaptation to other conductive metals is within the skill of the art, once the skilled worker is in possession of the teachings herein.

Plasmon Absorptivity

This is an optical parameter characterizing the metal core size of the particles in solution. For the gold based particles in dilute chloroform solution (0.4 mg/g chloroform), it is the 507 nm absorptivity normalized to a gram-atom of gold in the particle.

Resistance of Sensor Device

This parameter is a baseline from which modulations driven by vapor exposures occur. It is determined by both the resistivity of the particle thin film and the geometry of the electrode. The sensor device is fabricated by deposition of a particle thin film onto interdigital microelectrodes. The microelectrodes comprise a gold electrode array fabricated on a 7×12.5×1 mm quartz substrate and consist of 50 finger pairs with the following dimensions: spacing, 15 microns; finger width, 15 microns; overlap length, 4800 microns; electrode thickness, 1500 A. This device is mounted on a brass plate heated to 120° C. and coated with a 0.2 to 0.4 micron thick Au:$C_8$(1:1) film. Film deposition can be accomplished using an airbrush technique. In this case a 10 mg/ml chloroform solution is sprayed using a fine nozzle setting for 16 passes of one second duration. This produces a film with a thickness of 0.2 micron. Device resistances utilizing various particles as films deposited on the electrodes are entered in Table 1. Based on the above film thickness and electrode geometry, the film resistance (ohms) can be converted into a bulk material resistivity (ohm cm) by multiplying by a factor of 0.63. If the self-assembly film deposition technique is used, this conversion factor is not applicable since it incorporates a film thickness parameter.

Sensor Response to Vapors

This test refers to the magnitude of the modulation from the baseline resistance caused by exposure of the sensor device to a vapor. Resistivity (conductivity) changes in the sensor are measured using an AC technique. A square wave potential of 5 volts and a frequency of 100 hz is used to excite the microelectrode. The resulting current in the microelectrode is processed using a current-to-voltage converter circuit followed by a precision rectifier and low-pass filter. Thus, the magnitude of the 100 hz AC microelectrode current is converted into a proportional DC voltage. This voltage is converted to a frequency (using a V/F converter to allow data acquisition over a wide dynamic range using a computerized frequency counter). This measurement scheme allows the microelectrode current to be measured, displayed, and stored with a time resolution of one second and a relative current resolution of 0.001%. The sensor is mounted in a gold plated aluminum cell designed for low dead volume (i.e., <0.5 cc) with intake and exhaust ports positioned immediately above the electrode and connected to the circuit by way of pogo pin contacts to the contact pad of the electrode. Vapors of toluene, tetrachloroethylene, 1-propanol and water are generated from bubblers at 15° C., diluted with dry air to desired concentrations and delivered to the cell on an alternating exposure-purge schedule by a computer controlled vapor generator. An example of a typical sensor's responses to toluene vapor at 11,000 and 2.7 ppmv are illustrated in FIGS. 5 and 7, and the concentration dependencies are presented in FIG. 6. At the low end of the concentration range the dependence becomes nearly linear. As a single parameter to characterize and rank the responses of the different metal cluster films to individual vapors, the slope of the plot in FIG. 6 at a P/Po value of 0.10 is very useful. This parameter characterizes the sensitivity as well as the selectivity of a particular film of particles. A tabulation of this parameter is presented in Table 2 for the above cited vapors with sensors utilizing various particles.

Further information concerning embodiments and advantages of the claimed invention is set forth in the following examples and companion Tables 1 and 2. The characterizing features and test results reported in those Tables conform generally to the preceding discussion of test procedures and parameters.

EXAMPLE 1 (Au:SC8(1:1))

Solutions of: 4.56 g tetraoctylammonium bromide (($C_8H_{17}$)$_4$NBr) in 167 ml toluene; 0.8025 g (2.04 mmol) hydrogen tetrachloroaurate (III) trihydrate (HAuCl$_4$.3H$_2$O) in 62.5 ml distilled water; 0.297 g (2.03 mmol) 1-octanethiol ($C_8H_{17}$SH) in 2 ml toluene; and 0.7870 g sodium borohydride (NaBH$_4$) in 52.5 ml distilled water are prepared. With rapid stirring the AuCl$_4$/water solution is slowly added to the ($C_8H_{17}$)$_4$NBr/toluene solution. After 2 minutes the ($C_8H_{17}$SH)/toluene solution is added followed by the slow addition of the NaBH$_4$/water solution with very rapid stirring. The vigorous stirring is continued for 3 hr. The toluene phase is then separated and concentrated to a 10 ml volume at reduced pressure. The product is precipitated by dropwise addition into 800 ml rapidly stirred ethanol. After settling for several hours at 10° C., the supernate is decanted, and product is collected by centrifugation followed by washing with fresh ethanol and drying. This crude product is redissolved in 4 ml toluene and reprecipitated by dropwise addition into 200 ml rapidly stirred ethanol. After standing 12 hr at 10° C., the product is collected by centrifugation, washed with fresh ethanol and vacuum dried. The yield is 0.39 g. The gold mass fraction, core radius and 507 nm optical absorptivity characterization are presented in Table 1. A sensor fabricated by an airbrushed deposition of a thin film of this Au:C$_8$(1:1) particulate onto an interdigital microelectrode displays a baseline device resistance of 1.3 MΩ and 0.1 P/Po normalized resistance responses to toluene, tetrachloroethylene, 1-propanol and water vapors of 1.82, 1.45, −0.0514 and −0.0036 respectively (see Table 2).

EXAMPLE 2 (Au:SC8(1:3))

The Au:SC8(1:3) particle is prepared, fabricated into a sensor and tested as in Example 1 except utilizing a 1:3 mole ratio of HAuCl$_4$:$C_8H_{17}$SH. Characterization and sensor test results are presented in Tables 1 and 2.

EXAMPLE 3 (Au:SC8(3:1))

The Au:SC8(3:1) particle is prepared, fabricated into a sensor and tested as in Example 1 except utilizing a 3:1 mole ratio of HAuCl$_4$:$C_8H_{17}$SH. Characterization and sensor test results are presented in Tables 1 and 2

EXAMPLE 4 (Au:SC8(5:1))

The Au:SC8(5:1) particle is prepared, fabricated into a sensor and tested as in Example 1 except utilizing a 5:1 mole ratio of HAuCl$_4$:$C_6H_{17}$SH. Characterization and sensor test results are presented in Tables 1 and 2.

EXAMPLE 5 (Au:SC6(1:3))

The Au:SC6(1:3) particle is prepared, fabricated into a sensor and tested as in Example 1 except utilizing 1-hexanethiol ($C_6H_{13}$SH) in place of $C_8H_{17}$SH and a 1:3 mole ratio of HAUCl$_4$:$C_6H_{13}$SH. Characterization and sensor test results are presented in Tables 1 and 2.

EXAMPLE 6 (Au:SC6(1:1))

The Au:SC6(1:1) particle is prepared, fabricated into a sensor and tested as in Example 1 except utilizing 1-hexanethiol ($C_6H_{13}$SH) in place of $C_8H_{17}$SH and a 1:1 mole ratio of HAuCl$_4$:$C_6H_{13}$SH. Characterization and sensor test results are presented in Tables 1 and 2.

EXAMPLE 7 (Au:SC6(3:1))

The Au:SC6(3:1) particle is prepared, fabricated into a sensor and tested as in Example 1 except utilizing 1-hexanethiol ($C_6H_{13}$SH) in place of $C_8H_{17}$SH and a 3:1 mole ratio of HAuCl$_4$: $C_6H_{13}$SH. Characterization and sensor test results are presented in Tables 1 and 2.

EXAMPLE 8 (Au:SC6(5:1)).

The Au:SC6(5:1) particle is prepared, fabricated into a sensor and tested as in Example 1 except utilizing 1-hexanethiol ($C_6H_{13}$SH) in place of $C_8H_{17}$SH and a 5:1 mole ratio of HAuCl$_4$:$C_6H_{13}$SH. Characterization and sensor test results are presented in Tables 1 and 2.

EXAMPLE 9 (Au:SC4(1:1))

The Au:SC4(1:1) particle is prepared, fabricated into a sensor and tested as in Example 1 except utilizing 1-butanethiol ($C_4H_9$SH) in place of $C_8H_{17}$SH and a 1:1 mole ratio of HAuCl$_4$:$C_4H_9$SH. Characterization and sensor test results are presented in Tables 1 and 2.

EXAMPLE 10 (Au:SC12(1:1))

The Au:SC12 (1:1) particle is prepared, fabricated into a sensor and tested as in Example 1 except utilizing 1-dodecanethiol ($C_{12}H_{25}$SH) in place of $C_8H_{17}$SH and a 1:1 mole ration of HAuCl$_4$:$C_{12}H_{25}$SH. Characterization and sensor test results are presented in Tables 1 and 2.

EXAMPLE 11 (Au:SC12(3:1))

The Au:SC12(3:1) particle is prepared, fabricated into a sensor and tested as in Example 1 except utilizing 1-dodecanethiol ($C_{12}H_{25}$SH) in place of $C_8H_{17}$SH and a 3:1 mole ratio of HAuCl$_4$:$C_{12}H_{25}$SH. Characterization and sensor test results are presented in Tables 1 and 2.

EXAMPLE 12 (Au:SC12(5:1))

The Au:SC12(5:1) particle is prepared, fabricated into a sensor and tested as in Example 1 except utilizing 1-dodecanethiol ($C_{12}H_{25}$SH) in place of $C_8H_{17}$SH and a 5:1 mole ratio of HAuCl$_4$:$C_6H_{13}$SH. Characterization and sensor test results are presented in Tables 1 and 2.

EXAMPLE 13 (Au:SC12(8:1))

The Au:SC12(8:1) particle is prepared, fabricated into a sensor and tested as in Example 1 except utilizing 1-dodecanethiol ($C_{12}H_{25}$SH) in place of $C_8H_{17}$SH and a 8:1 mole ratio of HAuCl$_4$:$C_{12}H_{25}$SH. Characterization and sensor test results are presented in Tables 1 and 2.

EXAMPLE 14 (Au:SC16(5:1))

The Au:SC16(5:1) particle is prepared, fabricated into a sensor and tested as in Example 1 except utilizing hexadecanethiol ($C_{16}H_{33}$SH) in place of $C_8H_{17}$SH and a 5:1 mole ratio of HAuCl$_4$:$C_{16}H_{33}$SH. Characterization and sensor test results are presented in Tables 1 and 2.

EXAMPLE 15 (Au:St-C12(1:3))

The Au:St-C12(1:3) particle is prepared, fabricated into a sensor and tested as in Example 1 except utilizing a mixture of tertiary and primary decanethiol ($C_{16}H_{33}SH$) in place of $C_8H_{17}SH$ and a 1:3 mole ratio of $HAuCl_4:C_{12}H_{25}SH$. Characterization and sensor test results are presented in Tables 1 and 2.

EXAMPLE 16 (Au:St-C12(1:1))

The Au:St-C12(1:1) particle is prepared, fabricated into a sensor and tested as in Example 1 except utilizing a mixture of tertiary and primary decanethiol ($C_{16}H_{33}SH$) in place of $C_8H_{17}SH$ and a 1:1 mole ratio of $HAuCl_4:C_{12}H_{25}SH$. Characterization and sensor test results are presented in Tables 1 and 2.

EXAMPLE 17 (Au:SCPh(1:1))

The Au:SCPh(1:1) particle is prepared, fabricated into a sensor and tested as in Example 1 except utilizing benzyl mercaptan ($C_6H_5CH_2SH$) in place of $C_8H_{17}SH$ and a 1:1 mole ratio of $HAuCl_4:C_6H_5CH_2SH$. Characterization and sensor test results are presented in Tables 1 and 2.

EXAMPLE 18 (Au:SC2Ph(1:1))

The Au:SCPh2(1:1) particle is prepared, fabricated into a sensor and tested as in Example 1 except utilizing phenethyl mercaptan ($C_6H_5CH_2CH_2SH$) in place of $C_8H_{17}SH$ and a 1:1 mole ratio of $HAuCl_4:C_6H_5CH_2CH_2SH$. Characterization and sensor test results are presented in Tables 1 and 2.

EXAMPLE 19 (Au:SCPhOCH3(1:1))

The Au:SCPhOCH3(1:1) particle is prepared, fabricated into a sensor and tested as in Example 1 except utilizing 4-methoxybenzyl mercaptan ($CH_3OC_6H_4CH_2SH$) in place of $C_8H_{17}SH$ and a 1:1 mole ratio of $HAuCl_4:CH_3OC_6H_4CH_2SH$. Characterization and sensor test results are presented in Tables 1 and 2.

EXAMPLE 20 (Au:SPh(2:5))

The Au:SPh(2:5) particle is prepared as in Example 1 except utilizing thiophenol ($C_6H_5SH$) in place of $C_8H_{17}SH$ and a 2:5 mole ratio of $HAuCl_4:C_6H_5SH$. After the first precipitation this product is characterized by a low solubility in most organic solvents (chloroform, acetone, ethyl ether, tetrahydrofuran, toluene), and a second reprecipitation was not performed. A moderate solubility was found in chlorobenezene which was sufficient for the deposition procedure on the sensor electrode. The conductivity and vapor sensitivity test results are presented in Table 2.

EXAMPLE 21 (Au:SCPhOH(2:5))

Solutions of: 0.2983 g (0.757 mmol) $HAuCl_4.3H_2O$, 0.2285 g (1.812 mmol) 4-hydroxythiophenol ($HOC_6H_4SH$) and 3 ml acetic acid in 150 ml methanol; and 0.4510 g (11.9 mmol) sodium borohydride ($NaBH_4$) in 30 ml distilled water are prepared. The $NaBH_4$/water solution is added dropwise over a 5 min period to the $HAuCl_4/HOC_6H_4SH$/methanol solution with rapid stirring. Stirring is continued for 45 min. The reaction mixture is then concentrated at reduced pressure (20mm/35° C.) to a 2 to 3 ml volume and precipitated into 150 ml distilled water. The crude product is then washed with three 50 ml portions of water. The crude product is dissolved in 3 ml acetone and precipitated into 150 ml ethyl ether. This product is collected by centrifugation and dried. The yield is 63.5 mg. The conductivity and vapor sensitivity tests are presented in Table 2.

EXAMPLE 22 (Au:NC12(1:11))

Solutions of 0.2347 g (0.596 mmol) $HAuCl_4.3H_2O$ in 50 ml distilled water; 1.1930 g (6.44 mmol) 1-dodecylamine ($C_{12}H_{25}NH_2$) in 50 ml toluene; and 0.3592 g (9.50 mmol) sodium borohydride ($NaBH_4$) in 50 ml distilled water are prepared. The $C_{12}H_{25}NH_2$/toluene solution is added to the $HAuCl_4$/water solution with rapid stirring. After 5 min, a thick suspension is formed and the $NaBH_4$/water solution is added dropwise over a 10 min period. The rapid stirring is continued for 12 hr. The toluene phase is then separated and concentrated to a 3 ml volume at reduced pressure (20mm/35° C.). The product is precipitated by dropwise addition into 225 ml of rapidly stirred methanol, collected by centrifugation after standing for 3 hr and vacuum dried. The yield is 4.7 mg. A multiplicity of these particles is deposited as a thin film on the sensor electrode by way of the air brush technique using a chloroform solution. The conductivity and vapor sensitivity tests are presented in Table 2.

EXAMPLE 23 (Au:NC16(1:11))

The Au:NC16(1:11) particle is prepared and fabricated into a sensor as in Example 22 utilizing an equivalent molar quantity of 1-hexadecylamine ($C_{16}H_{33}NH_2$) in place of $C_{12}H_{25}NH_2$. An improved particle yield of 54.2 mg is obtained. The conductivity and vapor sensitivity tests are presented in Table 2.

EXAMPLE 24 (Au:NC18(1:11))

The Au:NC18(1:11) particle is prepared and fabricated into a sensor as in Example 22 utilizing an equivalent molar quantity of 1-octadecylamine ($C_{18}H_{37}NH_2$) in place of $C_{12}H_{25}NH_2$. A further improved yield of 133.2 mg is obtained. The conductivity and vapor sensitivity tests are presented in Table 2.

EXAMPLE 25 (Au:SC6(3:1)/Fluoropolyol Codeposition)

A solution of 17.9 mg Au:C6(3:1) particle materials (Example 7) and 2.6 mg FPOL (fluoroalcohol polymer investigated for dimethyl methyphosphonate (DMMP) sorption: see Snow, A. W. et al, J. Appl. Poly. Sci., 43, 1659 (1991)) are codissolved in 2.40 g chloroform. A sensor fabricated by an airbrushed deposition of a thin film of this polymer cluster composite onto an interdigital microelectrode (@120°) displays a baseline resistance of 0.018 megohms and 0.1 P/Po normalized resistance responses to toluene, 1-propanol and water vapors of 1.17, 0.258 and 0.0265 respectively (see Table 2). Sensitivity to DMMP at 0.0041 P/Po is 57 times greater than of the Au:C6(3:1) without the fluoropolyol.

EXAMPLE 26 (Au:SC4(1:1) Self-Assembled Deposition)

An electrode and quartz substrate is surface activated by chloroform immersion cleaning, immersion in a 5% sodium hydroxide solution for 10 min, thorough rinsing with distilled water and drying 2 hr at 120° C. Solutions of: 5.0 mg AuSC4(1:1) precursor materials (Example 9) in 1.00 g chloroform; 13.6 mg 1,8-octanedithiol in 1.02 g chloroform; and 6.0 mg 3-(dimethoxymethysilyl)-1 propanethiol in 0.5 g hexane (thiol-silane coupling agent solution) are prepared. After 2-hour drying at 120° C. the electrode is immediately immersed in the thiol-silane coupling agent solution for 1 hour. After removing the electrode and rinsing with hexane, it is immersed in the octanedithiol solution for 5 min. The activated device surface (electrode and substrate) is then rinsed with chloroform and alternately immersed in the Au:SC4(1:1) precursor material and octanedithiol solutions for a total of 21 cycles. Each cycle results in a conductivity increment corresponding to a current increase of approximately 400 nA. The deposited film is very uniform and not removable by immersion in a variety of organic solvents or by mild abrasion with a cotton swab. The conductivity and vapor sensitivity tests are presented in Table 2.

EXAMPLE 27 (Au:SC4(1:1) Self-Assembled Deposition)

An electrode and quartz substrate is surface activated by chloroform immersion cleaning followed by a reduced pressure oxygen plasma surface treatment utilizing a standard laboratory plasma cleaner. This treatment consists of three 5 sec leakages of small volumes of air at one minute intervals into an evacuated chamber containing the sensor electrode under a plasma discharging electric field. The deposition of the Au:SC4(1:1) particles then proceeds with the immersion in the thiol-silane coupling agent solution follow by the alternate immersions in the dithiol and Au:SC4(1:1) precursor material solutions as described in Example 26.

EXAMPLE 28 (Au:SC4(1:1) Self-Assembled Deposition)

The self-assembled deposition procedure in Example 27 is modified by substituting a 3-(trimethoxysilyl)-1-propanethiol coupling agent for the 3-(dimethoxymethylsilyl)-1-propanethiol coupling agent. The conductivity and vapor sensitivity test of this sensor are presented in Table 2.

EXAMPLE 29 (Au:SC6(1:1) Self-Assembled Deposition)

A sensor is fabricated with a self-assembled Au:SC6(1:1) deposition following the procedure in Example 26 except that Au:SCG(1:1) particles are substituted for the Au:SC4(1:1) particles and the number of deposition cycles is 22. The conductivity and vapor sensitivity tests of this sensor are presented in Table 2.

EXAMPLE 30 (Au:SC8(1:1) Self-Assembled Deposition)

A sensor is fabricated with a self-assembled Au:SC8(1:1) deposition following the procedure in Example 26 except that Au:SC8(1:1) particles are substituted for the Au:SC4(1:1) particles, and the number of deposition cycles is 28. The conductivity and vapor sensitivity tests of this sensor are presented in Table. 2.

EXAMPLE 31 (Condensed Phase)

An Au:SC8(1:1) sensor is fabricated as described in Example 1 and utilized to detect toluene dissolved in distilled water. The sensor is immersed in distilled water and then in toluene/water solutions at concentrations of 0.052 and 0.0052 weight percent. Responses of the sensor are measure under DC conditions with a constant bias potential of 0.105 V. The immersion in the distilled causes an increase in the baseline current from 40 to 180 nA. Subsequent immersion in the 0.052 weight % toluene/water solution causes the baseline current to decrease to 50 nA (a 72% decrease in current). Reimmersion in distilled water returns the baseline current to 180 nA. Four repetitions of these alternating immersions produce the same result. The same experiment conducted with the 0.0052 weight % toluene/water solution resulted in a 12% decrease in the sensor current.

EXAMPLE 32 (Condensed Phase)

An Au:SC4(1:1) sensor is fabricated as described in Example 28 and utilized to detect toluene dissolved in distilled water. The sensor is immersed in distilled water and then in toluene/water solutions at a concentration of 0.052 weight percent. Responses of the sensor are measured under DC conditions with a constant bias potential of 0.05 V. The immersion in the distilled causes an decrease in the baseline current from 6600 to 4400 nA. Subsequent immersion in the 0.052 weight % toluene/water solution causes the baseline current to further decrease to 4200 nA (a 4.5% decrease in current). Reimmersion in distilled water returns the baseline current to 4400 nA. Three repetitions of these alternating immersions produce the same result.

TABLE 1

Stabilized Particle Characterization

| Example | Particle | $W_{Au}$ | $R_{Core}$ (nm) | $\epsilon_{507}$ (1/mol Au cm) |
|---|---|---|---|---|
| 1 | Au:SC8(1:1) | 0.807 | 1.11 | 2190 |
| 2 | Au:SC8(1:3) | 0.751 | 0.63 | 1640 |
| 3 | Au:SC8(3:1) | 0.841 | 1.53 | 2410 |
| 4 | Au:SC8(5:1) | 0.904 | 3.01 | 2790 |
| 5 | Au:SC6(1:3) | 0.792 | 0.66 | 1560 |
| 6 | Au:SC6(1:1) | 0.824 | 0.96 | 1970 |
| 7 | Au:SC6(3:1) | 0.884 | 1.61 | 2510 |
| 8 | Au:SC6(5:1) | 0.919 | 2.92 | 2700 |
| 9 | Au:SC4(1:1) | 0.879 | 1.24 | 2200 |
| 10 | Au:SC12(1:1) | 0.755 | 1.14 | 2260 |
| 11 | Au:SC12(3:1) | 0.796 | 1.56 | 2550 |
| 12 | Au:SC12(5:1) | 0.871 | 2.97 | 2830 |
| 13 | Au:SC12(8:1) | 0.895 | 3.61 | 2970 |
| 14 | Au:SC16(5:1) | 0.835 | 2.83 | 2750 |
| 15 | Au:St-C12(1:3) | 0.828 | 1.25 | 2280 |
| 16 | Au:St-C12(1:1) | 0.871 | 2.90 | 2780 |
| 17 | Au:SCPh(1:1) | 0.838 | 1.18 | 2100 |
| 18 | Au:SC2Ph(1:1) | 0.810 | 1.04 | 2346 |
| 19 | Au:SC1PhOCH3(3:1) | 0.796 | 1.56 | 2550 |

TABLE 2

Sensor Response to Vapors

| | | Ro | $(DR/Ro)/(P/Po)_{0.10}$ | | | |
|---|---|---|---|---|---|---|
| Example | Particle | (Megohm) | Tol | TCE | PrOH | $H_2O$ |
| 1 | Au:SC8(1:1) | 1.3 | 1.82 | 1.45 | −0.051 | −0.0036 |
| 2 | Au:SC8(1:3) | 300 | 0.38 | 0.30 | −0.37 | −0.019 |
| 3 | Au:SC8(3:1) | 0.23 | 1.69 | 1.42 | −0.0077 | −0.0006 |

TABLE 2-continued

Sensor Response to Vapors

| Example | Particle | Ro (Megohm) | Tol | TCE | PrOH | $H_2O$ |
|---|---|---|---|---|---|---|
| | | | \multicolumn{4}{c}{$(DR/Ro)/(P/Po)_{0.10}$} |
| 4 | Au:SC8(5:1) | 0.11 | 1.58 | 1.40 | 0.22 | 0.020 |
| 5 | Au:SC6(1:3) | 20 | 1.31 | 1.07 | −0.012 | −0.0064 |
| 6 | Au:SC6(1:1) | 0.29 | 1.72 | 1.55 | 0.077 | −0.0057 |
| 7 | Au:SC6(3:1) | 0.0066 | 1.60 | 1.45 | −0.0035 | −0.0082 |
| 8 | Au:SC6(5:1) | 0.0025 | 0.87 | 1.04 | 0.064 | 0.0063 |
| 9 | Au:SC4(1:1) | 0.0047 | 0.80 | 0.94 | 0.0052 | 0.0013 |
| 10 | Au:SC12(1:1) | 140 | 0.48 | 0.36 | −0.096 | −0.018 |
| 11 | Au:SC12(3:1) | 32 | 0.98 | 0.78 | −0..015 | −0.0060 |
| 12 | Au:SC12(5:1) | 1.4 | 1.42 | 1.16 | 0.113 | 0.015 |
| 13 | Au:SC12(8:1) | 0.57 | 1.42 | 1.18 | 0.194 | 0.021 |
| 14 | Au:SC16(5:1) | 110 | 0.44 | 0.32 | 0.0026 | 0.0009 |
| 15 | Au:St-C12(1:3) | 0.27 | 1.26 | — | 0.25 | 0.019 |
| 16 | Au:St-C12(1:1) | 0.0013 | 0.66 | — | 0.053 | 0.0064 |
| 17 | Au:SCPh(1:1) | 0.0003 | 0.11 | — | 0.0311 | 0.0050 |
| 18 | Au:SC2Ph(1:1) | 0.031 | 1.85 | 1.58 | 0.045 | −0.0001 |
| 19 | Au:SC1PhOCH3(3:1) | 0.0026 | 0.624 | — | 0.14 | 0.0236 |
| 20 | Au:SPh(2:5) | 0.0011 | −0.049 | — | −0.0052 | −0.0001 |
| 21 | Au:SPhOH(2:5) | 990 | −0.0030 | — | −0.027 | −0.30 |
| 22 | Au:NC12(1:11) | 0.0016 | 0.87 | — | 0.34 | 0.11 |
| 23 | Au:NC16(1:11) | 0.069 | 1.26 | — | 0.13 | 0.015 |
| 24 | Au:NC18(1:11) | 0.29 | 1.03 | — | 0.12 | 0.023 |
| 25 | Au:SC6(3:1)/FPOL | 0.018 | 1.17 | — | 0.285 | 0.0265 |
| 26 | Au:SC4(1:1) S-A | 0.0049 | 0.47 | — | 0.085 | 0.019 |
| 27 | Au:SC4(1:1) S-A | 0.0071 | — | — | — | — |
| 28 | AuSC4(1:1) S-A | 0.0056 | 0.51 | — | — | — |
| 29 | AuSC6(1:1) S-A | 11 | 0.82 | — | 0.34 | 0.17 |
| 30 | AuSC8(1:1) S-A | 1.3 | 0.74 | — | 0.34 | 0.15 |

The invention described herein is susceptible of many modifications and variations within its scope, and in particular extends to the use of any one or more of the singular and several features of the foregoing description and accompanying drawings and their equivalents.

What is claimed is:

1. A method for investigating a target environment to determine whether or in what amount a chemical species may be present therein, which comprises
   (a) exposing to said environment an article of manufacture comprising a multiplicity of particles in close-packed orientation, said particles having a core of conductive metal or conductive metal alloy and deposited thereon a ligand which is capable of interacting with said species such that a property of said multiplicity of particles is altered;
   (b) subjecting said multiplicity of particles to conditions sufficient for said property to be exhibited; and
   (c) monitoring said property to determine whether there is, or the amount of, any change as an indication of whether, or in what amount, said species is present.

2. A method as defined in claim 1, wherein said core comprises silver, gold, platinum or palladium or an alloy of two or more of such metals.

3. A method as defined in claim 1, wherein said ligand shell comprises a substance which is capable of interacting with said species such that the conductivity of said multiplicity of particles is altered.

4. A method as defined in claim 1, wherein said ligand comprises a thiol or an amine.

5. A method as defined in claim 1, wherein in each said particle the core is of size from 0.8 to 40 nm in maximum dimension and the ligand shell is of thickness from 0.4 to 4.0 nm.

6. A method as defined in claim 1, wherein the particles are substantially spherical.

7. A method as defined in claim 1, wherein the species, when present, can be detected at an amount of 100 ppm or less.

8. A method for investigating a target environment to determine whether, or in what amount, a chemical species may be present, which comprises
   (a) exposing to said environment a multiplicity of particles having a core of conductive metal or conductive metal alloy, in each said particle the core being of from 0.8 to 40.0 nm in maximum dimension, and deposited on said core a ligand shell, of thickness from 0.4 to 4.0 nm, which is capable of interacting with said species such that the electrical conductivity of said multiplicity of particles is altered;
   (b) measuring the electrical conductivity of said multiplicity of particles to determine whether there has been, or the amount of, any change in such conductivity compared to the electrical conductivity of such particles not exposed to said environment.

9. A method as defined in claim 8, which comprises exposing the multiplicity of particles to said environment such that when the species is present the ligand shell absorbs said species and swells, with the result that the conductivity of the multiplicity of particles is changed.

10. A method as defined in claim 8, which comprises exposing the multiplicity of particles to said environment such that when the species is present the electronic charge distribution of the ligand shell is altered, with the result of the conductivity of the multiplicity of particles is changed.

11. A method as defined in claim 8, which further comprises comparing (a) the measurement of the conductivity of said multiplicity of particles exposed to said environment and (b) a contemporaneous measurement of the electrical conductivity of a comparable multiplicity of such particles not exposed to said environment.

* * * * *

UNITED STATES PATENT AND TRADEMARK OFFICE
CERTIFICATE OF CORRECTION

PATENT NO.      : 6,221,673 B1
DATED           : April 24, 2001
INVENTOR(S)     : Arthur W. Snow It is certified that error appears in the above-identified patent and that said Letters Patent is hereby corrected as shown below:

<u>Title page,</u>
Item [73], Assignee, insert:
-- The United States of America as represented by the Secretary of the Navy, Washington, D.C. -- after the current listing noting the first assignee.

Signed and Sealed this

Twenty-third Day of July, 2002

*Attest:*

*Attesting Officer*

JAMES E. ROGAN
*Director of the United States Patent and Trademark Office*